(12) United States Patent
Kritchevsky

(10) Patent No.: US 6,555,579 B2
(45) Date of Patent: *Apr. 29, 2003

(54) METHODS FOR REDUCING ATHEROSCLEROTIC PLAQUES

(75) Inventor: David Kritchevsky, Bryn Mawr, PA (US)

(73) Assignee: The Wistar Institute, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/673,493

(22) PCT Filed: Aug. 12, 1999

(86) PCT No.: PCT/US99/18505

§ 371 (c)(1),
(2), (4) Date: Mar. 16, 2001

(87) PCT Pub. No.: WO00/09118

PCT Pub. Date: Feb. 24, 2000

(65) Prior Publication Data

US 2003/0008920 A1 Jan. 9, 2003

Related U.S. Application Data

(60) Provisional application No. 60/096,352, filed on Aug. 13, 1998.

(51) Int. Cl.[7] ............................................. A61K 31/20
(52) U.S. Cl. ..................................................... 514/560
(58) Field of Search ........................................ 514/560

(56) References Cited

U.S. PATENT DOCUMENTS

| | | |
|---|---|---|
| 4,160,452 A | 7/1979 | Theeuwes |
| 4,256,108 A | 3/1981 | Theeuwes |
| 4,265,874 A | 5/1981 | Bonsen et al. |
| 4,857,516 A | 8/1989 | Terao et al. |
| 5,380,747 A | 1/1995 | Medford et al. |
| 5,760,082 A | 6/1998 | Cook et al. |
| 5,770,247 A | 6/1998 | Satter et al. |
| 5,814,663 A | 9/1998 | Cook et al. |
| 5,855,917 A | 1/1999 | Cook et al. |
| 5,856,149 A | 1/1999 | Pariza et al. |

OTHER PUBLICATIONS

Stanton et al., "Conjugated Linoleic Acid—A Marketing Advantage for Animal Fats," *Animal Fats—BSE & After*, Berger (ed.), 1997, PJ Barnes & Associates, Bridgewater, UK, Chapter 2, pp. 27–41.
Buchwald et al., *Am. J. Physiol.*, 1964, 207:567–572.
Buchwald, *Atherosclerosis*, 1983, 46:117–128.
Chin et al., *J. Food Comp. Anal.*, 1992, 5:185–197.
Dhiman et al., *J. Dairy Sci.*, 1996, 79(Suppl. 1):137.
Dormandy et al., *Chem. Phys. Lipids*, 1987, 45:353–364.
Duff et al., *J. Exp. Med.*, 1949, 89:611–630.
Fogarty et al., *Nutr. Rep. Intl.*, 1988, 38(5):937–944.
Garcia–Lopez et al., *Food Res. Intl.*, 1994, 27:61–64.
Genaro (ed.), *Remington's Pharmaceutical Sciences*, 1985, Mack Publishing Co., Easton, PA (Table of Contents Only).
Ha et al., *Carcinogenesis*, 1987, 8(12):1881–1887.
Ha et al., *J. Agric. Food Chem.*, 1989, 37:75–81.
Ip et al., *Cancer Res.*, 1991, 51(22):6118–6124.
Jiang et al., *J. Dairy Sci.*, 1996, 79(3):438–445.
Jiang, *Conjugated Linoleic Acid—Occurence, Oxidation and Production by Dairy Starter Cultures*, 1998, Swedish University of Agricultural Sciences, Uppsala, Sweden (Table of Contents only).
Kelly and Bauman, "Conjugated Linoleic Acid: A Potent Anticarcinogen Found in Milk Fat," *Proc. Cornell Nutr. Conference*, 1996, Syracuse, NY, Cornell University, Ithaca, NY, pp. 68–74.
Kepler et al., *J. Biol. Chem.*, 1967, 242(24):5686–5692.
Kritchevsky, *Lipid Pharmacology*, 1964, Academic Press, NY, Chapter 2, pp. 63–130.
Kritchevsky, *Hypolipidemic Agents*, 1975, Springer–Verlag, Berlin, Chapter 6, pp. 215–227.
Lawless et al., *J. Dairy. Sci.*, 1998, 81(12):3259–3267.
Lee et al., *Atherosclerosis*, 1994, 108:19–25.
Lin et al., *J. Dairy Sci.*, 1995, 78:2358–2365.
Munday et al., *Br. J. Nutrition*, 1999, 81:251–255.
Naito and Schwartz, *Nutrition and Heart Disease*, 1982, Spectrum Publications, NY, Chapter 1, pp. 1–25.
Nicolosi et al., *Artery*, 1997, 22(5):266–277.
Parodi, *J. Dairy Sci.*, 1977, 60(10):1550–1553.
Parodi, *Austral. J. Dairy Tech.*, 1994, 49:93–97.
Riel, *J. Dairy Sci.*, 1963, 46(2):102–106.
Rodrigueza et al., *Biochimica et Biophysica Acta*, 1998, 1368:306–320.
Shantha et al., *J. Agric. Food Chem.*, 1994, 42:1757–1760.
Shantha et al., *J. Amer. Oil Chem. Soc.*, 1994, 69(5):425–428.
Shantha et al., *J. Food Sci.*, 1995, 60(4):695–697.
Stanton et al., *J. Food Sci.*, 1997, 62(5):1083–1086.
Sugano et al., *J. Nutr. Biochem.*, 1997, 8:38–43.
Werner et al., *J. Agric. Food Chem.*, 1992, 40:1817–1821.
Wisler et al., *Ann. N.Y. Acad. Sci.*, 1976, 275:363–378.

Primary Examiner—Rebecca Cook
(74) Attorney, Agent, or Firm—Fish & Richardson P.C., P.A.

(57) ABSTRACT

A method for reducing atherosclerotic plaques includes administering an effective amount of at least one fatty acid composition to an animal, said fatty acid composition having a carbon chain of at least 16 carbons in length, and wherein at least one pair of double bonds are in a conjugated position. Such a method and article of manufactures facilitating these methods may be useful for reducing atherosclerotic plaques in humans.

39 Claims, No Drawings

METHODS FOR REDUCING ATHEROSCLEROTIC PLAQUES

This is a 37 of PCT/US99/18505 filed Aug. 12, 1999 which claim benefit of No. 60/096,352 filed Aug. 13, 1998.

FIELD OF THE INVENTION

The invention relates to reducing deposits in arteries. In particular, the invention relates to reducing atherosclerotic plaques using fatty acids.

BACKGROUND OF THE INVENTION

Atherosclerosis is one of the major vascular diseases affecting people throughout the world and has been defined by the World Health Organization as a "variable combination of changes of the intima of arteries (as distinct from arterioles) consisting of the focal accumulation of lipids, complex carbohydrates, blood and blood products, fibrous tissue and calcium deposits, and associated with medial changes." See "Classification of Atherosclerotic Lesions," Report of a Study Group Definition of Terms, W. H. O. Tech. Rep. Ser., 143:4 (1958).

Atherosclerosis in mammals is characterized by formation of atherosclerotic plaques or atherosclerotic lesions in large and medium-sized arteries. See, e.g., Naito & Schwartz, *Nutrition and Heart Disease*, pp. 1–25, Ed. Naito, Spectrum Publications, Jamaica, N.Y. (1982). Atherosclerotic plaques reduce the arterial lumen thereby reducing, obstructing or, in severe cases, stopping blood flow through the artery. The irregular surface of atherosclerotic plaques can lead to intra-arterial thrombi. Detachment of all or a portion of a thrombus from an atherosclerotic plaque can lead to obstruction of an artery located downstream from the plaque, resulting in localized tissue ischemia and/or stroke.

Early stages of atherosclerotic plaque formation are manifested as "fatty or lipid streaks" on arterial walls. These fatty streaks contain lipid-laden foam cells located in the subendothelial layer of the arterial intima. Additional intracellular and extracellular lipids accumulate at the site of the plaque during later plaque formation stages causing raised lesions. In addition, smooth muscle and connective tissue cells may migrate into the plaque and/or proliferate within the plaque. Plaques (sometimes referred to as atheromata) damage the intimal surface of the artery weakening the artery and decreasing its elasticity. Intimal damage may also attract additional cells and extracellular materials to accumulate at or near the plaque. Over time, a plaque may calcify. As cells and extracellular materials accumulate, the intimal surface of the artery becomes irregular, which may lead to the accumulation of blood platelets and thrombus formation. The committee on lesions of the American Heart Association has recognized from 6 to 8 different stages of plaque formation starting from the basically invisible lipid streaks, through the visible raised lesions and ending in a fully occluded artery. As such, atherosclerotic plaque formation is really a continuum of events.

Current methods for preventing atherosclerosis target reducing known risk factors. These risk factors include hypercholesterolemia, hypertension, tobacco smoking, obesity, physical inactivity, familial history, and (possibly) personality type. Prevention methods include reducing cholesterol and other fat intake, exercise, weight control, cessation of smoking, and monitoring of blood lipid levels. For example, it has been suggested that administering cholesterol-lowering or cholesterol-sequestering compounds and/or drugs, including conjugated linoleic acids may prevent the formation of atherosclerotic plaques. Lee et al., *Atherosclerosis*, 108:19–25 (1994); and Nicolosi et al., *Artery*, 22:266–277 (1997).

Once an atherosclerotic plaque has formed, and particularly once the plaque has become fibrous or infiltrated by smooth muscle cells, treating atherosclerotic plaques is complicated especially when the plaques cause significant obstruction of an artery. In fact, obstruction of coronary arteries by atherosclerotic plaques is one reason numerous coronary bypass surgical procedures are performed each year.

Current methods for treating existing atherosclerotic plaques are limited. Pharmaceutical or surgical approaches to atherosclerotic plaque diminution have only inconsistently resulted in minimal plaque regression. See, e.g. Buchwald et al., *New Eng. J. Med.*, 232:946–55 (1990); Rodrigueza et al., *Biochim. Biophys. Acta*, 1368:306–320 (1998); and Wissler et al., *Ann. N.Y. Acad. Sci.*, 275:363 (1976). Known physical methods for removing or reducing atherosclerotic plaques include angioplastic flattening of the atherosclerotic lesions, insertion of arterial stents, surgical excision of the plaque, ablation of a portion of the plaque (e.g., laser angioplasty), and replacement of an occluded artery with another artery or a vein obtained from the same patient (e.g., cardiac bypass surgery or mammary artery grafting).

These current physical methods exhibit severe limitations, costs and risks. For example, expanding a plaque-occluded artery by balloon angioplasty or surgically removing occluding material from such an artery often provides only temporary relief from atherosclerosis because the expanded or surgically invaded artery often quickly returns to the pre-surgical reduced lumenal diameter. In fact, about 40% of the arteries subjected to angioplasty reocclude. Furthermore, removing lipid and other material adhering to an arterial wall can release particles that travel through the bloodstream and occlude cerebral blood vessels or reduce cerebral blood flow causing a stroke. Surgical or angioplastic intervention at the site of an atherosclerotic plaque may also further weaken already compromised vascular tissues, increasing the likelihood of hemorrhage or aneurysm. Surgical grafting of an artery or vein obtained from elsewhere in the patient's body do not tend to lengthen the life expectancy of patients relative to similarly afflicted patients who do not undergo such the surgery. Furthermore, grafted blood vessels are also likely to become re-occluded.

As such, despite advances in the preventing, detecting, and treating of atherosclerotic plaques, coronary artery disease, atherosclerotic heart disease and complications related to these disease states remain leading causes of death. Accordingly, there exists a need for non-invasive methods for treating existing atherosclerotic lesions in humans.

SUMMARY OF THE INVENTION

In one aspect, the invention features a method for reducing atherosclerotic plaques that includes administering an effective amount of at least one polyunsaturated fatty acid composition to a mammal such as a human. The fatty acid composition can have a carbon chain of at least 16 carbons in length and at least one pair of double bonds in a conjugated position. In one embodiment, the fatty acid composition is a mixture of different fatty acids with some of the fatty acids being at least $C_{16}$ fatty acids having one or more pairs of conjugated double bonds.

In some embodiments, the effective amount of the fatty acid composition can be altered. Useful effective amount concentrations include amounts ranging from about 0.01% to about 5% of a total diet on a weight by weight basis, from about 0.01% to about 1% of a total diet on a weight by weight basis, or from about 0.01% to about 0.5% of a total diet on a weight by weight basis. For example, the effective amount can be about 0.01%, about 0.025%, about 0.05%, about 0.1%, about 0.5%, or about 1.0% of a total diet on a weight by weight basis.

The effective amount may also be measured directly. The effective amount may be given daily or weekly or fractions thereof. For example, in some embodiments the effective amount is a fatty acid dose that ranges from about 1 milligram to about 25 grams of the fatty acid composition per day, about 50 milligrams to about 10 grams of the fatty acid composition per-day, from about 100 milligrams to about 5 grams of the fatty acid composition per day, about 1 gram of the fatty acid composition per day, about 1 milligram to about 25 grams of the fatty acid composition per week, about 50 milligrams to about 10 grams of the fatty acid composition per week, about 100 milligrams to about 5 grams of the fatty acid composition every other day, and about 1 gram of the fatty acid composition once a week.

In another embodiment, the method is used in conjunction with a total diet that is a low-cholesterol diet or a cholesterol-free diet.

In some embodiments, the method includes a polyunsaturated fatty acid composition containing a fatty acid having a carbon chain length greater than 16 carbons. Other embodiments can use fatty acids having carbon chain lengths ranging from 16 carbons in length to 22 carbons in length, inclusive. For example, the carbon chains of the fatty acids may be 16, 17, 18, 19, 20, 21, or 22 carbons in length or longer. In some embodiments, the fatty acid is conjugated linoleic acid.

The fatty acid composition may include a lipophilic entity, a pharmaceutical composition, a foodstuff, a nutraceutical, or any other suitable means for providing the fatty acid composition to a mammal. Foodstuffs can be a fat or oil containing foodstuff, such as the foodstuffs selected from the group consisting of animal meat, ruminant animal meat, ruminant mammal milk, and vegetable oil. Other foodstuffs can be, for example, a vegetable starch, a vegetable protein, a vegetable fiber, or an emulsified salad dressing.

The fatty acid composition may be in the form of a monoglyceride, diacylglyceride, triacylglyceride, free fatty acid, or fatty acid ethyl ester. In addition, the fatty acid composition may be a specific fatty acid such as 9,11-octadecadienoic acid, 10,12-octadecadienoic acid, 11,13-octadecadienoic acid, and any geometric isomers thereof. The fatty acid composition can be a mixture of two or more fatty acids such as a mixture of 9,11-octadecadienoic acid and 10,12-octadecadienoic acid and any geometric isomers thereof. Mixtures of fatty acids can be present in equal proportions on a weight by weight basis. For example, 9,11-octadecadienoic acid and 10,12-octadecadienoic acid can be present at about equal proportions on a weight by weight basis. The fatty acid composition can be or can include a specific fatty acid isomer such as 9,11-octadecadienoic acid or 10,12-octadecadienoic acid and any geometric isomers thereof, e.g., c9,t11-octadecadienoic acid or t10,c12-octadecadienoic acid.

In some embodiments, the fatty acid composition contains a fatty acid having at least three double bonds or at least four double bonds, wherein at least two of the double bonds are conjugated.

The methods disclosed herein can be effective for reducing atherosclerotic plaques in an artery, such as an aortic artery, a coronary artery, a carotid artery, and a cerebral artery.

The invention also features an article of manufacture including:
a) packaging material; b) at least one polyunsaturated fatty acid composition contained within the packaging material, wherein the fatty acid composition is effective for administration to a mammal, the fatty acid composition having a carbon chain of at least 16 carbons in length, and wherein the fatty acid composition has at least one pair of double bonds in a conjugated position; and c) a label or package insert contained with the packaging material indicating that the fatty acid composition is effective for administration to the mammal so as to reduce atherosclerotic plaques in the mammal. The label or package insert may also indicate that administering the enclosed fatty acid composition to a human is effective for reducing atherosclerotic plaques in a human. The fatty acid composition may include a fatty acid having a carbon chain of 18 carbons in length. Alternatively, the article of manufacture can be used in conjunction with any of the fatty acid compositions disclosed herein.

Additional aspects or embodiments of the invention include the following examples, which may be used in conjunction with the aspects of the invention described above.

A further aspect the invention includes methods for administering fatty acid compositions in the form of a lipophilic entity. The compositions may be pharmaceutical compositions and/or nutraceutical compositions each of which can contain a lipophilic entity that further includes a conjugated linoleic acid moiety. Lipophilic entities may be selected from free fatty acids, fatty acid esters, glycerides, phosphoglycerides, phosphatidylglycerides, phosphatidylcholine glycerides, phosphatidylethanolamine glycerides, phosphatidylserine glycerides, phosphatidylinositides, diphosphatidylglycerides, sphingolipids, ceramides, sphingomyelins, glucocerebrosides, and phrenosides.

In one embodiment, the fatty acid composition includes at least one conjugated octadecadienoic acid. The conjugated octadecadienoic acid may be selected from the group consisting of 9,11-octadecadienoic acid, 10,12-octadecadienoic acid, and all geometric isomers thereof. In another embodiment, the composition includes a mixture of at least two conjugated octadecadienoic acids. When a mixture is used, it may be preferable that at least about 40 mole percent of the at least two conjugated octadecadienoic acids is c9,t11-octadecadienoic acid and at least about 40 mole percent of the at least two conjugated octadecadienoic acid is t10,c12-octadecadienoic acid.

The invention also features a method for reducing atherosclerotic plaques by administering a pharmaceutical composition containing a conjugated fatty acid to a human at a dose ranging from about 1 milligram per day to about 25 grams per day. In another aspect, the invention features a method for reducing atherosclerotic plaques by administering a foodstuff containing a nutraceutical composition containing a conjugated fatty acid to a human at a dose ranging from about 1 milligram per day to about 25 grams per day. The foodstuff may be naturally-occurring and may include a lipophilic entity. The foodstuff may be selected from the group consisting of animal meat, ruminant animal meat, animal milk, and ruminant animal milk. The nutraceutical may be a foodstuff prepared using naturally-occurring ingredients supplemented with a lipophilic entity. The ingredients may be selected from the group consisting of animal meat, ruminant animal meat, animal milk, ruminant animal milk, vegetable starch, vegetable protein, vegetable fiber, and vegetable oil.

In another aspect, the invention features an article of manufacture or kit for reducing atherosclerotic plaques in a human afflicted with atherosclerosis. The kit includes a package containing a fatty acid composition in the form of a lipophilic entity. The kits may be used with any of the fatty acid compositions described herein. The compositions may be pharmaceutical compositions and/or nutraceutical compositions each of which can contain a lipophilic entity that further includes a conjugated linoleic acid moiety. In one embodiment, the kit includes a package containing a naturally-occurring foodstuff that contains a naturally-occurring amount of a lipophilic entity that includes a conjugated linoleic acid moiety.

The kits further include at least one indicium that discloses that the composition is useful and/or effective for diminishing atherosclerotic plaques in a human. The indicium may, for example, be selected from the group consisting of text borne by the package, an image borne by the package, text borne by an insert within the package, an image borne by an insert within the package, text borne by a point-of-sale display shipped with the package, an image borne by a point-of-sale display shipped with the package, text borne by a point-of-sale display displayed together with the package, and an image borne by a point-of-sale display displayed together with the package.

In one embodiment, the pharmaceutical composition included in a kit further includes a pharmaceutically acceptable carrier. In another embodiment, the pharmaceutical composition is selected from the group consisting of a tablet, a hard capsule, a soft capsule, a cachet, a troche, a lozenge, a powdered formulation, a granular formulation, an aqueous suspension, an oily suspension, an aqueous solution, an oily solution, an emulsion in an oily vehicle, an emulsion in an aqueous vehicle, a suppository, a retention enema preparation, a solution for rectal or colonic irrigation, a suppository, an impregnated vaginally-insertable material, a coated vaginally-insertable material, a douche preparation, a solution for vaginal irrigation, a paste, an implantable sustained-release formulation, a biodegradable formulation, a liniment, a lotion, a cream, an ointment, a paste, and eye drops.

The pharmaceutical and/or nutraceutical compositions may be in unit doses. The doses may include from about 50 milligrams to about 5 grams of the lipophilic entity. The doses may range from about 0.01% to about 50% by weight of a conjugated linoleic acid moiety. The lipid content of the contents of the kit may range from about 0.01% to about 100% by weight of the lipid content of the nutraceutical composition is the conjugated linoleic acid moiety.

In another aspect, the invention features a method for diminishing atherosclerotic plaques in a human afflicted with atherosclerosis wherein the method includes the steps of increasing consumption of naturally-occurring foodstuffs containing lipophilic entities containing conjugated linoleic acid moieties.

Unless otherwise defined, all technical and scientific terms used herein have the same meaning as commonly understood by one of ordinary skill in the art to which this invention belongs. As used herein, the term "include(s)" is illustrative and is equivalent to the phrase "include(s), but is not limited to." Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The methods described herein are useful for treating and preventing atherosclerotic plaques. In particular, atherosclerotic plaques can be reduced by administering an effective amount of at least one polyunsaturated fatty acid or fatty acid composition to a mammal. A polyunsaturated fatty acid is a fatty acid having at least two double bonds and may have three, four, five, or six or more double bonds. As used herein, a fatty acid composition is a composition containing at least one fatty acid and that is suitable for administration to a mammal. An important aspect of these methods is that the fatty acid has at least one pair of double bonds that are conjugated. These methods can be used alone or in conjunction with other known methods for treating atherosclerotic plaques. As used herein, atherosclerotic plaques and/or lesions include any and all stages of atherosclerotic plaque formation including, for example, fatty or lipid streaks, raised lesions, atheroma, fibrous plaques, and calcified plaques.

Reducing atherosclerotic plaques includes both preventing the formation of new atherosclerotic plaques and/or reducing the size of existing atherosclerotic plaques. Reducing plaque size can include reducing (i) the percentage of the surface area affected by atherosclerotic plaque in one or more arteries of a mammal, (ii) the number of plaques found in one or more arteries of a mammal, and/or (ii) the severity of such plaques. The size and/or severity of atherosclerotic plaques may be assessed using methods known to those of ordinary skill in the art. Plaque severity may be assessed by embedding and sectioning an affected artery and then visualizing plaque severity using computer-aided visualization techniques. In addition, the size and/or severity of atherosclerotic plaques can be measured as percent occlusion of the artery, which is determined using angiography or other known means for visualizing arteries. Atherosclerotic plaque reduction may occur in specific arteries such as aortic arteries, coronary arteries, carotid arteries, and cerebral arteries.

Any fatty acid (including naturally occurring and chemically synthesized fatty acids) having at least one pair of double bonds in a conjugated position may be used. Two double bonds, i.e., a pair, are conjugated when they are separated by only one carbon—carbon bond, i.e., no methylene groups separating the double bonds. The fatty acids used herein may have more than two double bonds per fatty acid chain. Preferred fatty acids include fatty acids having carbon backbones of at least 16 carbons in length and in particular, carbon backbones ranging from 16 carbons ($C_{16}$) to 22 carbons ($C_{22}$) in length, inclusive. Fatty acids having 18 carbon ($C_{18}$) backbones are specifically contemplated. The fatty acids may have one or more pairs of conjugated double bonds in any geometric or positional isomer. Geometric isomers of fatty acids include double bonds in the cis and trans configuration. Each fatty acid double bond may exist in either the cis or the trans geometric conformation. Positional isomers refer to the location of the double bond along the carbon backbone. Fatty acid double bonds may occur anywhere along the carbon backbone between the second carbon ($C_2$) and the penultimate carbon ($C_{n-1}$) wherein n represents the total number of carbons in the fatty acid chain. Thus, there exists a large number of isomers for each fatty acid. As used herein, referring to a fatty acid without designating a particular geometric or positional isomer is meant to refer to all possible geometric and positional isomers for that fatty acid.

A preferred fatty acid is octadecadienoic acid ($C_{18}H_{32}O_2$), which also is known as dienyl octadecanoic acid. Octadecadienoic acid may exist in a large number of geometric and positional isomeric forms. The possible positional isomers for octadecadienoic acid are represented generically by Chemical Formula (I) wherein the sum of a, d, and e is 13, and wherein each of a, d, and e is an integer from 0 to 13. It is to be understood that each double bond may also exist in either the cis or trans configuration, i.e., geometric isomers.

(Formula I)

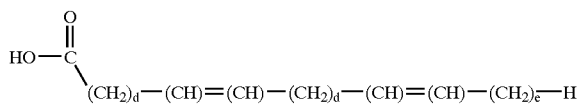

One naturally occurring isomer of octadecadienoic acid is octadeca-9-12-dienoic acid. Chemical Formula II shows an isomer of octadeca-9-12-dienoic acid when both double bonds are in the trans configuration, i.e., octadeca-t9-t12-dienoic acid.

(Formula II)

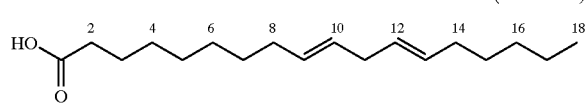

Linoleic acid is the trivial name for the isomer of octadeca-9-12-dienoic acid when both double bonds are in the cis configuration, i.e., octadeca-c9-c12-dienoic acid and is shown in Chemical Formula III. Octadeca-t9-t12-dienoic acid may also be referred to as linoleic acid, however, the cis:cis form is more prevalent.

(Formula III)

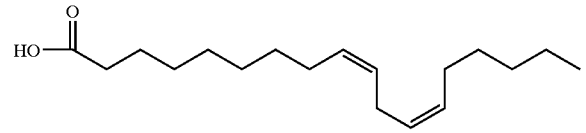

Conjugated linoleic acid (CLA) is a term used in the art when referring to a modified linoleic acid where the double bonds are in a conjugated form. That is, CLA refers to octadeca-9-11-dienoic acid and octadeca-10-12-dienoic acid and all possible geometrical isomers thereof, i.e., cis:trans; cis:cis; trans:cis; and trans:trans. The octadeca-9-11-dienoic acid species has also been referred to as rumenic acid. Although other isomers have been reported, the principal species found in nature so far is octadeca-c9-t11-dienoic acid. CLA is commercially available from multiple sources, including, for example, Nu-Chek-Prep, Inc., Elysian, Minn., and is sold under the tradename Tonalin brand CLA(TM) by Natural Lipids Limited A. S., Hovdebygda, Norway.

Fatty acids including CLA occur naturally in animal tissue, animal fluids and may be found in vegetable tissue and vegetable fluids. Typically, animals provide the primary sources of CLA. Accordingly, many foods provide a source of CLA and other fatty acids. For example, ruminant animal meat, cheese, milk and other dairy products are rich sources of CLA. See, e.g., Parodi, *Austral. J. Dairy Tech.*, 49:93–97 (1994); Ha et al., *J. Agric. Food Chem.*, 37:75–81 (1989); Chin et al., *J. Food Comp. Anal.*, 5:185–197 (1992); Ip et al., *Cancer Res.*, 51:6118–6124 (1991); Shantha et al., *J. Food Sci.*, 60:695–697 (1995); Fogerty et al., *Nutr. Rep. Intl.*, 38:937–944 (1988); Shantha et al., *J. Amer. Oil Chem. Soc.*, 69:425–428 (1994); Werner et al., *J. Agric. Food Chem.*, 40:1817–1821 (1992); and Lin et al., *J. Dairy Sci.*, 78:2358–2365 (1995).

Food processing methods can enhance the fatty acid and/or CLA content of a foodstuff. Suitable methods for enhancing the CLA content of a foodstuff include Ha et al., *Carcinogenesis*, 8:1881–1887 (1987); Garcia-Lopez et al., *Food Res. Intl.*, 27:61–64 (1994); Shantha et al., *J. Amer. Oil Chem. Soc.*, 69:425–428 (1994); Shantha et al., *J. Agric. Food Chem.*, 42:1757–1760 (1994); Werner et al., *J. Agric. Food Chem.*, 40:1817–1821 (1992); Lin et al., *J. Dairy Sci.*, 78:2358–2365 (1995); and Jiang, "Conjugated Linoleic Acid—Occurrence, Oxidation and Production by Dairy Starter Cultures, Ph.D. Thesis, Swedish University of Agricultural Sciences, Uppsala Sweden (1998). Also, the fatty acid and/or CLA content can be increased through the use of food excipients such as cooking oils and non-stick sprays.

Furthermore, increasing the CLA content of an animal or vegetable may enhance the CLA content of food products derived from such animals or vegetables. Methods for enhancing the CLA content of an animal or vegetable are known and include the methods described in U.S. Pat. No. 5,770,247 "Method of Increasing the CLA Content of Cow's Milk"; Stanton et al., *J. Food Sci.*, 62:1083–1086 (1997); Lawless et al., *J. Dairy Sci.*, 81(12):3259–67 (1998); Jiang et al., *J Dairy Sci.*, 79:438 (1996); Dhiman et al., *J. Dairy Sci.*, 79(Suppl.1):137 (1996); Kelly et al., "Conjugated Linoleic Acid: A Potent Anticarcinogen Found in Milk Fat", *Proc. Cornell Nutr. Conf.*, Syracuse, N.Y., Cornell Univ., Ithaca, N.Y. (1996); Parodi, *J. Dairy Sci.*, 60:1550 (1977); Stanton et al., *Animal Fats: BSE and After*, Berger, Ed., P. J. Barnes and Assoc., Bridgwater, U.K., pp. 27–41 (1997); and Riel, *J. Dairy Sci.*, 46:102–106) (1963).

Alternatively, CLA and other fatty acid isomers may be produced synthetically using known methods. Suitable methods for producing CLA and conjugated fatty acids in general include the methods described in U.S. Pat. No. 5,856,149 "Method of Producing Conjugated Fatty Acids." Other methods for producing CLA include exposing linoleic acid to a bacterial linoleic acid isomerase, such as that obtained from *Butyrivibrio fibrisolvens*, as described in Kepler et al., *J. Biol. Chem.* 242:5606–5609 (1967), treating linoleic acid with base and heat for a period of time and then neutralizing the mixture as described in U.S. Pat. No. 5,760,082, and exposing linoleic acid to a free radical-generating species in the presence of at least one sulfur-rich protein as described in Dormandy et al., *Chem. Phys. Lipids*, 45:353–364 (1987).

Accordingly, foodstuffs and nutraceutical compositions containing increased concentrations of at least one fatty acid and/or increased concentrations of at least one CLA can be prepared by following the methods described herein. As used herein, a "foodstuff" includes any composition that is processed into or used as food, preferably by a human. As used herein, a "nutraceutical" is a foodstuff that has physiological activity beyond that of the foodstuff. A foodstuff or nutraceutical composition has an enhanced fatty acid and/or CLA level when it contains at least one fatty acid and/or CLA at a concentration greater than that at which it naturally occurs in the foodstuff. Such foodstuffs may be prepared by adding a fatty acid and/or CLA to a foodstuff or substituting at least one fatty acid and/or CLA for another in a foodstuff, by selecting ingredients that contain higher levels of the particular fatty acid and/or CLA.

A foodstuff preferably contains from about 0.1% to about 50% (w/w) CLA. The lipid content of the foodstuff preferably contains from about 0.1% to about 100% (w/w) CLA. More preferably, the foodstuff, or the lipid content thereof, includes at least about 1% (w/w) CLA. It is to be understood that the lipid content of the foodstuff may be adjusted, using known food processing methods, to substantially any value between about 0.1% to about 100% (w/w) CLA. It is further understood that the lipid content of the foodstuff will depend upon the lipid content of the ingredients of the foodstuff prior to processing, the degree of processing considered desirable, the effect upon palatability of varying the CLA content, and other factors readily ascertainable by the skilled artisan.

The fatty acid and/or CLA may be used in any form including as a free fatty acid, fatty acid ethyl ester, fatty acid amide or derivatives thereof, salt, monoglyceride, diglyceride, or triglyceride. Any fatty acid modifications should result in a physiologically acceptable composition. As used herein, the term "physiologically acceptable" ester or salt means an ester or salt form of the active ingredient that is compatible with the other ingredients of a foodstuff or pharmaceutical composition and which is not deleterious to the subject receiving the fatty acid composition.

Fatty acids of the invention can be in any form including a free fatty acid, a fatty acid ester, fatty acid amide or derivatives thereof, a glyceride, a phosphoglyceride, a phosphatidylglyceride, a phosphatidylcholine glyceride, a phosphatidylethanolamine glyceride, a phosphatidylserine glyceride, a phosphatidylinositide, a diphosphatidylglyceride, a sphingolipid, a ceramide, a sphingomyelin, a glucocerebroside, a phrenoside, and the like. Any fatty acid may be converted into a lipophilic entity by modifying a free fatty acid with a lower alky, glycerol, a glyceride, a phosphoglycerol, a phosphoglyceride, an alkyl glyceryl ether, or a sphingosine substituent. A lipophilic entity of this type is described herein as a "lipophilic entity which includes a CLA moiety." As used herein, "lower alkyl" includes straight and branched chain alkyls having from one to about six carbon atoms, inclusive. Glycerides include glycerol substituted at one or more hydroxyl residues with an acyl substituent, such as a fatty acid. Phosphoglycerols include glycerol substituted at a hydroxyl residue with a substituent selected from the group consisting of phosphatidic acid, phosphatidylcholine, phosphatidylethanolamine, phosphatidylserine, phosphatidylinositide a phosphatidylglyceride, or another phosphatidylglycerol molecule. Phosphoglycerides include phosphoglycerols in which the glycerol is substituted at another hydroxyl residue with an acyl moiety, such as a fatty acid. Sphingosine substituents include sphingosine, dihydrosphingosine, O-phosphocholine-sphingosine, and O-glycosphingosines.

A lipophilic entity that contains a fatty acid moiety may be used in the form of a homogenous preparation of the lipophilic entity or as an emulsion of the lipophilic entity in an aqueous liquid (e.g. a lipophilic entity-in-water emulsion, a water-in-lipophilic entity emulsion, or a liposomal preparation of the lipophilic entity). The use of lipophilic entities containing more than one fatty acid isomer are expressly contemplated. Furthermore, the use of multiple lipophilic entities, each containing one or more fatty acid isomers is contemplated. Examples of multiple lipophilic entities include mixtures of CLA fatty acid isomers, diglycerides or triglycerides having the same or different acyl CLA substituents, liposomes containing a CLA fatty acid and a CLA ester, and the like.

Fatty acids and/or CLA may also be administered to a mammal in the form of a pharmaceutical composition containing a fatty acid and/or CLA as the active ingredient. Such a pharmaceutical composition may contain only the active ingredient. The pharmaceutical composition may also contain the active ingredient together with one or more pharmaceutically acceptable carriers, one or more additional ingredients, and even other active ingredients. Administering these pharmaceutical compositions to a mammal may reduce or diminish atherosclerotic plaques in the mammal.

A "pharmaceutically acceptable carrier" is a chemical composition with which the active ingredient may be combined and which, following the combination, can be used to administer the active ingredient to a subject. Pharmaceutically acceptable carriers are known to those of ordinary skill in the art.

Pharmaceutical compositions described herein may be prepared by any known method or method developed hereafter in the art of pharmacology. In general, such preparatory methods include the step of combining an active ingredient with a carrier and/or one or more other accessory ingredients, and then, if necessary or desirable, shaping or packaging the product into a desired single- or multi-dose unit.

Although the pharmaceutical compositions provided herein are principally directed to those suitable for ethical administration to humans, it is understood that such compositions are generally suitable for mammals of all sorts. The ordinarily skilled veterinary pharmacologist can design and perform any modifications needed to render the pharmaceutical compositions suitable for delivery to non-human mammals.

The pharmaceutical compositions may be prepared, packaged, or sold in any form that will introduce a fatty acid and/or CLA into the bloodstream of a mammal. Thus, pharmaceutical compositions of the invention include, formulations suitable for oral, parenteral, topical, buccal, or any other route of administration. Preferably, the pharmaceutical composition is formulated for oral delivery. Other contemplated formulations include projected nanoparticles, liposomal preparations, and resealed erythrocytes containing the active ingredient. Controlled- or sustained-release formulations of the pharmaceutical composition of the invention may be made using conventional technology.

A pharmaceutical composition of the invention may be prepared, packaged, or sold in bulk, as a single unit dose or as a plurality of single unit doses. As used herein, a "unit dose" is a discrete amount of the pharmaceutical composition, which includes a predetermined amount of the active ingredient. The amount of the active ingredient is generally equal to the active ingredient dose that would be administered to a subject or a convenient fraction thereof, e.g., ½ dose or ⅓ dose.

The relative amounts of the active ingredient, pharmaceutically acceptable carrier, and any additional ingredients in a pharmaceutical composition of the invention will vary, depending upon the identity, size, and condition of the subject treated. The relative amounts may further depend on the route by which the composition is to be administered. For example, the composition may contain from about 0.1% to about 100% (w/w) active ingredient. A unit dose of a pharmaceutical composition of the invention will generally contain from about 1 milligram to about 25 grams of the active ingredient, and preferably contains from about 50 milligrams to about 5 grams of the active ingredient.

Oral formulations may be prepared, packaged, and/or sold as a discrete solid dose unit such as a tablet, a hard or soft capsule, a cachet, a troche, or a lozenge, each containing a predetermined amount of the active ingredient. Other oral formulations include powdered or granular formulations, aqueous or oily suspensions, aqueous or oily solutions, and emulsions. As used herein, an "oily" liquid is a carbon-containing liquid molecule that exhibits a less polar character than water.

Tablets containing a fatty acid may be made by compressing or molding, in a suitable device, the active ingredient(s) alone or together with one or more additional ingredients. Compressed tablets may be prepared by compressing the active ingredient, when it is in a free-flowing form such as a powder or granular preparation, alone or together with one or more binders, lubricants, excipients, surface active agents, or dispersing agents. Molded tablets may be made by molding a mixture of the active ingredient, a pharmaceutically acceptable carrier, and sufficient liquid to moisten the mixture. Pharmaceutically acceptable excipients used for manufacturing tablets include inert diluents, granulating and disintegrating agents, binding agents, and lubricating agents. Known dispersing agents include potato starch and sodium starch glycollate. Known surface active agents include sodium lauryl sulphate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets may be non-coated or coated so as to achieve delayed disintegration of the tablet in the gastrointestinal tract of a subject. Coating tablets may provide sustained release and absorption of the active ingredient. Glyceryl monostearate or glyceryl distearate may be used to coat tablets. Methods for coating tablets are known and include the methods described in U.S. Pat. Nos. 4,256,108; 4,160,452; and 4,265,874 for forming osmotically-controlled release tablets. Tablets may include sweetening agents, flavoring agents, coloring agents, preservatives, or combinations thereof.

Hard capsules and soft gelatin capsules containing an active ingredient may be manufactured using a physiologically degradable composition, such as gelatin. Hard capsules can further include inert solid diluents such as calcium carbonate, calcium phosphate, and kaolin.

Soft gelatin capsules containing an active ingredient may be manufactured using a physiologically degradable composition, such as gelatin. Such soft capsules contain the active ingredient, which may be mixed with water or an oil medium such as peanut oil, liquid paraffin, or olive oil.

Liquid pharmaceutical formulations that are suitable for oral administration may be prepared, packaged, and sold in liquid form or as a dry product intended for reconstitution with water or another suitable vehicle before ingestion. Liquid suspensions may be prepared using known methods for suspending the active ingredient in an aqueous or oily vehicle. Aqueous vehicles include water and isotonic saline. Oily vehicles include almond oil, oily esters, ethyl alcohol, vegetable oils (e.g., arachis, olive, sesame, or coconut oil), fractionated vegetable oils, and mineral oils (e.g., liquid paraffin). Liquid suspensions may further include one or more suspending agents, dispersing or wetting agents, emulsifying agents, demulcents, preservatives, buffers, salts, flavorings, coloring agents, and sweetening agents. Oily suspensions may further include a thickening agent. Known suspending agents include sorbitol syrup, hydrogenated edible fats, sodium alginate, polyvinylpyrrolidone, gum tragacanth, gum acacia, and cellulose derivatives (e.g., sodium carboxymethylcellulose, methylcellulose, hydroxypropylmethylcellulose). Known dispersing or wetting agents include naturally-occurring phosphatides such as lecithin. Dispersing or wetting agents also include condensation products of alkylene oxide with fatty acids, long chain aliphatic alcohol, partial esters derived fatty acids and hexitol, or partial esters derived from a fatty acid and hexitol anhydride (e.g. polyoxyethylene stearate, heptadecaethyleneoxycetanol, polyoxyethylene sorbitol monooleate, and polyoxyethylene sorbitan monooleate). Known emulsifying agents include lecithin, monoglycerides, and diglycerides. Known preservatives include methyl, ethyl, and n-propyl-para-hydroxybenzoates, ascorbic acid, and sorbic acid. Known sweetening agents include glycerol, propylene glycol, sorbitol, sucrose, and saccharin. Known thickening agents for oily suspensions include beeswax, hard paraffin, and cetyl alcohol.

Liquid solutions of the active ingredient in aqueous or oily solvents may be prepared in substantially the same manner as liquid suspensions, except that the active ingredient is dissolved rather than suspended in the solvent. Liquid solutions may include each of the components described for liquid suspensions with it being understood that suspending agents will not necessarily aid dissolution of the active ingredient in the solvent. Aqueous solvents include water and isotonic saline. Oily solvents include almond oil, oily esters, ethyl alcohol, vegetable oils such as arachis, olive, sesame, or coconut oil, fractionated vegetable oils, and mineral oils such as liquid paraffin.

Powdered and granular pharmaceutical compositions may be prepared using known methods. Such formulations may be administered directly to a subject or used, for example, to form tablets, fill capsules, or prepare aqueous or oily suspensions or solutions by adding an aqueous or oily vehicle thereto. Powdered and granular pharmaceutical compositions may further include one or more dispersing or wetting agents, suspending agents, preservatives, or excipients (e.g., fillers, sweetening agents, flavoring agents, and coloring agents).

Pharmaceutical compositions of the invention may also be prepared, packaged, or sold in the form of oil-in-water emulsion or a water-in-oil emulsion. The oily phase may be a vegetable oil (e.g., olive or arachis oil), a mineral oil (e.g., liquid paraffin), or a combination thereof. Emulsions may further include one or more emulsifying stabilizing agents such as gum acacia or gum tragacanth, phosphatides such as soybean or lecithin phosphatide, esters or partial esters derived from combinations of fatty acids and hexitol anhydrides such as sorbitan monooleate, and condensation products of partial esters with ethylene oxide such as polyoxyethylene sorbitan monooleate. Emulsions may also contain additional ingredients such as sweetening agents and flavoring agents.

As used herein, "parenteral administration" is characterized by administering a pharmaceutical composition through a physical breach of a subject's tissue. Parenteral administration includes administering by injection, through a surgical incision, or through a tissue-penetrating non-surgical wound, and the like. In particular, parenteral administration includes subcutaneous, intraperitoneal, intravenous, intraarterial, intramuscular, intrasternal injection, and kidney dialytic infusion techniques.

Parenteral formulations can include the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Parenteral administration formulations include suspensions, solutions, emulsions in oily or aqueous vehicles, pastes, reconsitutable dry (i.e. powder or granular) formulations, and implantable sustained-release or biodegradable formulations. Such formulations may also include one or more additional ingredients including suspending, stabilizing, or dispersing agents. Parenteral formulations may be prepared, packaged, or sold in the form of a sterile injectable aqueous or oily suspension or solution. Parenteral formulations may also include dispersing agents, wetting agents, or suspending agents described herein. Methods for preparing these types of formulations are known. Sterile injectable formulations may be prepared using non-toxic parenterally-acceptable diluents or solvents, such as water, 1,3-butane diol, Ringer's solution, isotonic sodium chloride solution, and fixed oils such as synthetic monoglycerides or diglycerides. Other parentally-administrable formulations include microcrystalline forms, liposomal preparations, and biodegradable polymer systems. Compositions for sustained release or implantation may include pharmaceutically acceptable polymeric or hydrophobic materials such as emulsions, ion exchange resins, sparingly soluble polymers, and sparingly soluble salts.

Pharmaceutical compositions may be prepared, packaged, or sold in a buccal formulation. Such formulations may be in the form of tablets, powders, aerosols, atomized solutions, suspensions, or lozenges made using known methods, and may contain from about 0.1% to about 20% (w/w) active ingredient with the balance of the formulation containing an orally dissolvable or degradable composition and/or one or more additional ingredients as described herein. Preferably, powdered or aerosolized formulations have an average particle or droplet size ranging from about 0.1 nanometers to about 200 nanometers when dispersed.

As used herein, "additional ingredients" include one or more of the following: excipients, surface active agents, dispersing agents, inert diluents, granulating agents, disintegrating agents, binding agents, lubricating agents, sweetening agents, flavoring agents, coloring agents, preservatives, physiologically degradable compositions (e.g., gelatin), aqueous vehicles, aqueous solvents, oily vehicles and oily solvents, suspending agents, dispersing agents, wetting agents, emulsifying agents, demulcents, buffers, salts, thickening agents, fillers, emulsifying agents, antioxidants, antibiotics, antifungal agents, stabilizing agents, and pharmaceutically acceptable polymeric or hydrophobic materials. Other "additional ingredients" which may be included in the pharmaceutical compositions are known. Suitable additional ingredients are described in *Remington's Pharmaceutical Sciences,* Mack Publishing Co., Genaro, ed., Easton, Pa. (1985).

Any of the free fatty acids, lipophilic entities, foodstuffs, nutraceuticals, and pharmaceutical compositions or formulations described herein may be administered according to the methods described herein to supplement the diet of a mammal. For example, an adult human may eat about 500 grams of solid food per day. A fatty acid may be added to an adult human diet to provide from about 1 milligram to about 25 grams of an additional fatty acid per day to the adult human and any particular value therebetween. Other useful ranges for fatty acid doses include from about 5 milligrams to about 10 grams per day, from about 50 milligrams to about 5 grams per day, about 50 milligrams per day, about 500 milligrams per day, about 1000 milligrams per day, about 1 gram per day, about 5 grams per day, about 10 grams per day, and about 15 grams per day. It is to be understood that mammals other than humans may require other dose ranges adjusted to the body size and metabolism differences according to each species. Also, the fatty acid dose may vary according to other factors such as the mammal's age, health, and/or severity of existing atherosclerotic plaques. For example, CLA may be administered to an adult human at a dose ranging from about 1 milligram to about 25 grams per day or any particular value therebetween such as about 1 or about 5 grams per day.

Fatty acid doses may also be administered as a percentage of a mammal's total diet. The lipid content of a mammal's diet may include from about 0.01% to about 100% of a lipid derived from a conjugated fatty acids described herein or any particular value therebetween. The conjugated fatty acid may range from about $2 \times 10^{-4}$% of a mammal's total diet to about 5% of a mammal's total diet or any particular value therebetween. Other useful ranges for fatty acid doses include from about 0.001% to about 5% of a mammal's total diet, from about 0.01% to about 5% of a mammal's total diet, from about 0.01% to about 2% of a mammal's total diet, and from about 0.1% to about 1% of a mammal's total diet. For example, about 0.01%, about 0.025%, about 0.1, about 0.5, about 1, about 2, about 3, about 4%, or about 5% of a mammal's total diet can be used. CLA may be administered to a human at a dose ranging from, for example, about $2 \times 10^{-4}$% of the human's total diet to about 5% of the human's total diet per day or any particular value therebetween such as about 0.01% or about 1% of the human's total diet per day. The human's total diet can be a low-cholesterol or cholesterol-free diet. A low-cholesterol diet contains less than about 300 mg of cholesterol per day (e.g., 100 mg of cholesterol per day). A cholesterol-free diet contains less than about 50 mg of cholesterol per day. It may also be useful to vary the length of time that the conjugated fatty acid is administered to the mammal. For example, it may be useful to supplement the mammal's diet once a week instead of every day, or to supplement the mammal's diet every other day.

The ordinarily skilled clinician can determine and prescribe an effective amount of a fatty acid to reduce atherosclerotic plaques in a subject using the methods described herein. To do so, the physician or veterinarian may, for example, prescribe a relatively low dose at first, subsequently increasing the dose until an appropriate response is obtained. It is further understood, however, that the specific dose level for any particular subject may depend upon a variety of factors including the specific activity of the fatty acid and/or particular isomer thereof used in the method. Other factors include the subject's age, body weight, general health, gender, and diet, the time of administration, the route of administration, the rate of excretion, other drugs or fatty acids used in combination, and the severity or extent of the subject's atherosclerotic plaques.

Any mammal including rats, mice, hamsters, rabbits, cats, dogs, pigs, sheep, cows, horses, primates and humans may benefit from the methods described herein. The mammals may receive the fatty acid in any of the forms described herein. The mammals may undergo treatment before or after an atherosclerotic plaque is detected. It may be advantageous to administer fatty acids as described herein to mammals having high risk factors for developing atherosclerotic plaques. The methods may be continued until the atherosclerotic plaques disappear from the mammal, or even longer, in order to take advantage of the anti-atherogenic properties of fatty acids having conjugated double bonds. A mammal receiving a fatty acid as described herein can be referred to as the subject.

Methods for reducing atherosclerotic plaques in a mammal can facilitate novel methods for doing business and novel articles of manufacture. For example, a fatty acid that is effective for reducing atherosclerotic plaques in a mammal when administered in an effective amount is manufactured, sold or offered for sale. The fatty acid can be in any form including a free fatty acid, a modified fatty acid, a fatty acid in a foodstuff, or a fatty acid in a pharmaceutical composition. Advertisements, marketing strategies, or other suitable promotions concerning the fatty acid are disseminated to a relevant audience. Suitable advertisements include radio and television advertisements, labels or other indicia present on packages containing fatty acids, promotional meetings, random or directed mailings, hand bills, and any other form of communication directed to the relevant audience. The relevant audience can include health care professionals such as doctors, nutritionists, counselors, and physician assistants, and/or the consuming public. The advertisements indicate that ingesting the fatty acids offered for sale can reduce atherosclerotic plaques in a mammal such as a human. The advertisements can further indicate that one of the useful fatty acids can be CLA. Such methods are useful for marketing or selling fatty acids and compositions containing fatty acids to consumers wanting to reduce atherosclerotic plaques in a mammal.

An article of manufacture can include packaging material and at least one fatty acid with the packaging material. The fatty acid contains at least one polyunsaturated fatty acid composition having a carbon chain of at least about 16 carbons in length, and wherein at least one pair of double bonds are in a conjugated position. The fatty acid, when ingested in an effective dose, is effective for reducing atherosclerotic plaques in a mammal. The packaging material includes a label, package insert or other indicia indicating that administering an effective amount of the fatty acid can reduce or diminish atherosclerotic plaques in a mammal such as a human. Any known packaging and printing method may be used to prepare the packaging material of the article of manufacture.

The article of manufacture can include the fatty acid in any form including a free fatty acid, a pharmaceutical or a nutraceutical composition of the invention.

As used herein, "indicia" or an "indicium" includes text, publications, recordings, images, diagrams, or any other tangible medium of expression or communication. The indicia may describe an appropriate dose of a free fatty acid, pharmaceutical or nutraceutical composition. The indicia may be affixed to, printed on, packed with, partially or entirely surround, stamped, or otherwise formed in the article of manufacture. The indicium may be shipped with or separately from the article of manufacture.

The invention will be further described in the following examples, which do not limit the invention as set forth in the claims.

EXAMPLE 1

Prevention of Atherosclerotic Plaque Formation

Rabbits, including New Zealand White rabbits, are an art-recognized model of atherosclerosis. See, e.g., Kritchevsky, *Lipid Pharmacology,* Paoletti, Ed., Academic Press, pp. 65–130 (1964); Kritchevsky, *Hypolipidemic Agents,* Kritchevsky, Ed., Springer Verlag, pp. 216–227 (1975). Rabbits have been used as a model of human atherosclerosis since early in the twentieth century. Accordingly, thirty male New Zealand white rabbits were fed an atherogenic diet ("control diet") for ninety days. The composition of the pelleted control diet is shown in Table 1. The composition of the vitamin and salt mixes of Table 1 is listed in Tables 1A and 1B, respectively.

Ten additional New Zealand white rabbits were fed the control diet supplemented with 1% w/w of a CLA composition ("Control+CLA diet"). The CLA composition, as provided by the manufacturer, is described in Table 1C. The Control+CLA diet also had the sucrose content adjusted to 20.3% to accommodate the addition of the CLA composition. The CLA composition was added to the control diet by a screw mixer but any method for combing the feed with the fatty acid source could have been used.

TABLE 1

Control Diet

| Ingredient | % (w/w) | % of Calories |
|---|---|---|
| Casein | 25.0 | 25.6 |
| DL-Methionine | 0.3 | — |
| Sucrose | 21.3 | 21.8 |
| Corn starch | 20.0 | 20.4 |
| Coconut Oil | 13.0 | 29.9 |
| Corn Oil | 1.0 | 2.3 |
| Cellulose | 14.0 | — |
| Salt mix | 4.0 | — |
| Vitamin mix | 1.0 | — |
| Choline bitartrate | 0.2 | — |
| Cholesterol | 0.2 | — |

TABLE 1A

Vitamin Mix

| Ingredient | Grams Ingredient/Kilogram Mix |
|---|---|
| Thiamin HCL | 0.6 |
| Riboflavin | 0.6 |
| Pyridoxine HCl | 0.6 |
| Niacin | 18.0 |
| Calcium Pantothenate | 1.6 |
| Folic Acid | 0.2 |
| Biotin | 0.02 |
| Vitamin $B_{12}$ (0.1% w/w) | 1.0 |
| Vitamin A Palmitate (500,000 IU/gm) | 0.8 |
| Vitamin $D^3$ (400,000 IU/gm) | 0.25 |
| Vitamin E Acetate (500 IU/gm) | 10.0 |
| Menadione Sodium Bisulfite | 0.08 |
| Sucrose | 966.25 |

TABLE 1B

Salt Mix

| Ingredient | Grams Ingredient/Kilogram Mix |
| --- | --- |
| Calcium Carbonate | 68.6 |
| Calcium Citrate | 306.19 |
| Calcium Phosphate, monobasic | 112.8 |
| Magnesium Carbonate | 35.2 |
| Magnesium Sulfate, anhydrous | 38.3 |
| Potassium Chloride | 124.7 |
| Potassium Phosphate, dibasic | 218.8 |
| Sodium Chloride | 77.1 |
| Ferric Ammonium Citrate | 15.28 |
| Cupric Carbonate | 0.04 |
| Manganese Sulfate | 0.20 |
| Aluminum Ammonium Sulfate | 0.09 |
| Potassium Iodide | 0.04 |
| Sodium Fluoride | 0.51 |
| Chromium Potassium Sulfate | 0.55 |
| Zinc Carbonate | 1.6 |

TABLE 1C

CLA Composition

| CLA Composition | % Weight Basis (% W:W) of Individual Isomers in CLA Composition |
| --- | --- |
| c9,t11-octadecadienoic acid | 43.3 |
| t10,c12-octadecadienoic acid | 45.3 |
| c9,c11-octadecadienoic acid | 1.9 |
| c10,c12-octadecadienoic acid | 1.4 |
| Mixture of t9,t11-octadecadienoic acid & t10,t12-octadecadienoic acid | 2.6 |
| Mixture of t9,c11-octadecadienoic acid & c10,t12-octadecadienoic acid | 1.1 |
| Linoleic Acid (c9,c12-octadecadienoic acid) | 4.4 |

The rabbits were maintained on their respective diets for 90 days, at which time, blood samples were collected from each rabbit. The thirty rabbits were then divided into three groups of ten rabbits. Each of the three groups of rabbits had an average serum cholesterol level of about 430 mg/dl. One of the three groups of rabbits were sacrificed. For each of the rabbits, plasma lipid and liver lipid levels were assessed, and each aorta was recovered and graded for severity of atherosclerotic lesions using a scale of 0 to 4 according to the methods described in Duff & McMillan, *J. Exp. Med.*, 89:611–630 (1949). The extent of atheroma formation was assessed in terms of the percentage of the lumenal aortic surface affected by one or more atherosclerotic lesions. The ten rabbits that received the Control+CLA diet were also sacrificed and analyzed according to the Duff & McMillan methods used for the control rabbits. The necropsy results are shown in Table 2.

TABLE 2

Necropsy Results

| | Control Diet | Control + CLA Diet | % Change |
| --- | --- | --- | --- |
| Serum Cholesterol | | | |
| Total (mg/dl) | 505 ± 33 | 430 ± 40 | 15% Decrease |
| HDL (%) | 6.1 ± 0.4 | 3.6 ± 0.5 | 41% Decrease |
| Triglycerides (mg/dl) | 83 ± 4 | 135 ± 36 | 63% Increase |
| Atherosclerosis Score | | | |
| Arch | 2.39 ± 0.47 | 1.65 ± 0.37 | 31% Decrease |
| Thoracic | 2.35 ± 0.36 | 1.40 ± 0.40 | 40% Decrease |
| Atherosclerotic area (%) | 49 ± 10 | 30 ± 10 | 39% Decrease |

Table 2 indicates that rabbits fed the Control+CLA diet had significantly lowered total and HDL cholesterol levels relative to rabbits fed the Control diet. Furthermore, rabbits fed the Control+CLA diet exhibited less atherosclerosis relative to rabbits fed the control diet.

EXAMPLE 2

Reducing the Severity of Existing Atherosclerotic Plaques

The remaining two groups of ten rabbits (Group 1 & Group 2) (20 rabbits total) of Example 1 were fed different diets to determine if a fatty acid composition could reduce or diminish existing atherosclerotic plaques. Group 1 was fed a cholesterol-free diet ("Regression diet") that contained 6% corn oil, as shown in Table 3. Group 2 was fed the same regression diet except that the corn oil content was adjusted to 5.0% (w/w). The diet fed to Group 2 further contained the CLA composition of Example 1 at a concentration of 1% (w/w) of the diet ("Regression+CLA diet").

TABLE 3

Regression Diet

| Ingredient | % (w/w) | % of Calories |
| --- | --- | --- |
| Casein | 24.0 | 26.2 |
| DL-Methionine | 0.3 | — |
| Sucrose | 30.6 | 33.4 |
| Corn starch | 23.5 | 25.7 |
| Cellulose | 14.0 | — |
| Corn oil | 6.0 | 14.7 |
| Salt mix | 0.4 | — |
| Vitamin mix | 1.0 | — |
| Choline bitartrate | 0.2 | — |

The rabbits were maintained on their respective diets for an additional 90 days. After ninety days, each rabbit was sacrificed and underwent the lipid and atherosclerotic lesion analysis described in Example 1. The Necropsy results are shown in Table 4.

TABLE 4

Necropsy Results

| | Regression Diet | Regression + CLA Diet | % Change |
| --- | --- | --- | --- |
| Serum Cholesterol | | | |
| Total (mg/dl) | 73 ± 10 | 140 ± 24 | 92% Increase |
| HDL (%) | 13.5 ± 1.0 | 13.1 ± 1.1 | 3% Decrease |
| Triglycerides (mg/d) | 66 ± 9 | 57 ± 5 | 14% Decrease |

TABLE 4-continued

Necropsy Results

| | Regression Diet | Regression + CLA Diet | % Change |
|---|---|---|---|
| Atherosclerosis Score | | | |
| Arch | 2.35 ± 0.35 | 1.65 ± 0.26 | 30% Decrease |
| Thoracic | 2.30 ± 0.40 | 1.65 ± 0.22 | 28% Decrease |
| Atherosclerotic area (%) | 51 ± 11 | 34 ± 6 | 33% Decrease |

Table 5 shows that although the serum cholesterol levels were reduced in rabbits fed the Regression diet, the pre-existing atherosclerotic plaques were not reduced or diminished by eating the Regression diet. Surprisingly, pre-existing atherosclerotic plaques were reduced in rabbits fed the Regression+CLA diet.

TABLE 5

| | Regression Diet | Regression + CLA Diet |
|---|---|---|
| % change versus Control | | |
| Arch Atherosclerotic Score | 2% Reduction | 31% Reduction |
| Thoracic Ather. Score | 1% Reduction | 30% Reduction |
| % of Lumenal Aortic Surface Area Affected by Atheroma | 4% Increase | 31% Reduction |

As indicated in Tables 4 and 5, the surface area of the aorta affected by atherosclerotic plaques was reduced by about one third in rabbits fed the Regression+CLA diet relative to rabbits fed either the Control diet or the Regression diet. Furthermore, the aortic atherosclerotic score for rabbits maintained on the Regression+CLA diet was reduced relative to the aortic score of rabbits maintained on either the Control diet or the Regression diet. These results indicate that adding a conjugated fatty acid such as CLA to the diet can reduce the extent and severity of pre-existing atherosclerotic plaques. The results presented in Table 5 further indicate that the observed reductions in the extent and severity of atherosclerosis were not due to the absence of cholesterol in the diet because the Regression diet lacked cholesterol and yet the atherosclerotic plaques remained essentially unchanged relative to these properties in rabbits maintained on the Control diet.

The results indicate that adding CLA to a human diet will reduce the extent and severity of atherosclerotic plaques in humans. It is understood that the anti-atherosclerotic efficacy of adding CLA to a human diet may be improved if the diet is also relatively low in cholesterol, meaning that the diet includes no more than about 200–300 milligrams cholesterol daily. In particular, a low-cholesterol diet would include about 100 milligrams of cholesterol or less per day. It is anticipated that an anti-atherosclerotic effect will be observed by adding a conjugated fatty acid such as CLA to a human diet in an amount ranging from about 0.01% (w/w) of the total diet to about the maximum tolerated dose, preferably in an amount of about 0.1%–5% (w/w), and more preferably in an amount of about 1% (w/w).

EXAMPLE 3

Induction and Reduction of Atherosclerotic Plaques

The extent and severity of atherosclerotic plaques in rabbits was assessed using a two phase study. Phase I was a progression phase where atherogenic lesions were induced. Phase II was a regression phase where rabbits having pre-existing atherogenic lesions were maintained on cholesterol-free diets supplemented with CLA. Three different CLA concentrations measured on weight by weight (w:w) basis were tested. The CLA levels were 0.1%, 0.5%, and 1%.

Four groups of ten rabbits (collectively group I) were fed the atherogenic diet of Example I supplemented with CLA at a concentration of 0.0%, 0.1%, 0.5%, or 1.0%, by weight. Forty additional rabbits (group II) were fed the atherogenic diet of Example I without any additional CLA being added. All 64 rabbits were maintained on their respective diets for 120 days. Eight rabbits died for reasons unrelated to the experiment.

After 120 days, the group I rabbits (8 rabbits) were sacrificed and analyzed according the methods used in Examples 1 & 2 (Duff & McMillan). The results are shown in Table 6 and Table 7.

TABLE 6

CLA Effect on Induction and Prevention of Atherosclerosis (Necropsy Results)

| | % CLA | | | |
|---|---|---|---|---|
| | 0.0 | 0.1 | 0.5 | 1.0 |
| Serum Cholesterol | | | | |
| Total | 983 ± 118 | 1281 ± 116 | 1263 ± 104 | 1103 ± 134 |
| % HDL | 5.01 ± 0.90 | 3.3 ± 0.54 | 3.3 ± 0.58 | 5.0 ± 1.14 |
| Triglycerides | 190 ± 32 | 246 ± 27 | 205 ± 48 | 216 ± 38 |
| Atherosclerosis Score | | | | |
| Arch | 2.36 ± 0.39 | 1.69 ± 0.23 | 0.88 ± 0.20 | 1.00 ± 0.28 |
| Thoracic | 2.21 ± 0.42 | 1.31 ± 0.38 | 0.75 ± 0.20 | 0.94 ± 0.27 |
| Area | 44 ± 12 | 32 ± 7 | 11 ± 4 | 18 ± 6 |

TABLE 7

Percentage Change Due to CLA for Induction and Prevention of Atherosclerosis (Necropsy Results)

| | % CHANGE | | | |
|---|---|---|---|---|
| | 0.0% CLA | 0.1% CLA | 0.5% CLA | 1.0% CLA |
| Serum Cholesterol | | | | |
| Total | CONTROL | 30% Increase | 28% Increase | 12% Increase |
| % HDL | CONTROL | 34% Decrease | 34% Decrease | 0% Increase |
| Triglycerides | CONTROL | 29% Increase | 8% Increase | 14% Increase |
| Atherosclerosis Score | | | | |
| Arch | CONTROL | 28% Decrease | 63% Decrease | 58% Decrease |
| Thoracic | CONTROL | 41% Decrease | 66% Decrease | 57% Decrease |
| Area | CONTROL | 27% Decrease | 75% Decrease | 59% Decrease |

The group II rabbits were separated into four groups of approximately the same average blood cholesterol level as in Example 2. Each group was maintained on a cholesterol-free diet (Regression Diet) as in Example II. Each group was supplemented with a different concentration of CLA. The CLA concentrations were 0.0%, 0.1%, 0.5%, and 1% by weight. The rabbit groups were as follows: 7 rabbits (0.0%), 6 rabbits (0.1%), 7 rabbits (0.5%), and 6 rabbits (1%). The rabbits were fed the regression diets for an additional 90 days. After 90 days, the rabbits were assessed according to the methods described for Examples I and II (Duff & McMillan). The results are shown in Table 8 and Table 9.

TABLE 8

CLA Effect on Regression of Atherosclerosis (Necropsy Results)

| | % CLA | | | |
|---|---|---|---|---|
| | 0.0 | 0.1 | 0.5 | 1.0 |
| Serum Cholesterol | | | | |
| Total | 128 ± 38 | 140 ± 19 | 295 ± 48 | 309 ± 46 |
| % HDL | ND | ND | ND | ND |
| Triglycerides | 47 ± 7 | 61 ± 8 | 124 ± 8 | 105 ± 20 |
| Atherosclerosis Score | | | | |
| Arch | 2.64 ± 0.28 | 2.25 ± 0.28 | 2.50 ± 0.29 | 1.92 ± 0.40 |
| Thoracic | 2.29 ± 0.36 | 2.33 ± 0.44 | 2.00 ± 0.15 | 1.25 ± 0.17 |
| Area | 53 ± 7 | 53 ± 10 | 49 ± 5 | 30 ± 10 |

ND = not determined

TABLE 9

Percentage Change Due to CLA for Regression of Atherosclerosis (Necropsy Results)

| | % CHANGE | | | |
|---|---|---|---|---|
| | 0.0% CLA | 0.1% CLA | 0.5% CLA | 1.0% CLA |
| Serum Cholesterol | | | | |
| Total | CONTROL | 9% Increase | 130% Increase | 141% Increase |
| % HDL | CONTROL | ND | ND | ND |
| Triglycerides | CONTROL | 34% Increase | 164% Increase | 123% Increase |
| Atherosclerosis Score | | | | |
| Arch | CONTROL | 15% Decrease | 5% Decrease | 27% Decrease |
| Thoracic | CONTROL | 2% Increase | 13% Decrease | 45% Decrease |
| Area | CONTROL | 0% | 8% Decrease | 43% Decrease |

ND = not determined

EXAMPLE 4

Induction and Reduction of Atherosclerotic Plagues

Example 3 is repeated substituting a substantially pure fraction of c9,t11-octadecadienoic acid for the CLA composition found in Table 1C. A substantially pure fraction is a fatty acid composition that contains less than about 10% of any other fatty acid isomers in the composition. It is to be understood that Example 4 can be repeated with any fatty acid isomer. Furthermore, the isomer does not have to be substantially pure but instead could be a mixture of two or more fatty acids.

While the invention described herein may reference specific embodiments, it is to be understood that other aspects, embodiments, advantages, and variations of the invention may be devised by others skilled in the art without departing from the invention. Accordingly, other aspects, advantages, and modifications are within the scope of the following claims.

What is claimed is:

1. A method for reducing atherosclerotic plaques in a mammal comprising administering an effective amount of a composition comprising at least one polyunsaturated fatty acid compound to said mammal, said fatty acid compound having a carbon chain of at least 16 carbons in length, and wherein said fatty acid compound has at least one pair of double bonds in a conjugated position.

2. The method of claim 1 wherein said effective amount ranges from about 0.01% to about 5% of a total diet on a weight by weight basis.

3. The method of claim 2 wherein said effective amount ranges from about 0.01% to about 1% of a total diet on a weight by weight basis.

4. The method of claim 2 wherein said effective amount ranges from about 0.01% to about 0.5% of a total diet on a weight by weight basis.

5. The method of claim 2 wherein said effective amount is about 1.0% of a total diet on a weight by weight basis.

6. The method of claim 2 wherein said effective amount is about 0.5% of a total diet on a weight by weight basis.

7. The method of claim 2 wherein said total diet comprises a low-cholesterol diet.

8. The method of claim 2 wherein said total diet comprises a cholesterol-free diet.

9. The method of claim 1 wherein said carbon chain ranges from 16 carbons in length to 22 carbons in length.

10. The method of claim 1 wherein said carbon chain is 16 carbons in length.

11. The method of claim 1 wherein said carbon chain is 18 carbons in length.

12. The method of claim 1 wherein said carbon chain is 20 carbons in length.

13. The method of claim 1 wherein said effective amount ranges from about 1 milligram to about 25 grams of said composition per day.

14. The method of claim 1 wherein said effective amount ranges from about 50 milligrams to about 10 grams of said composition per day.

15. The method of claim 1 wherein said effective amount ranges from about 100 milligrams to about 5 grams of said composition per day.

16. The method of claim 1 wherein said effective amount is about 1 gram of said composition per day.

17. The method of claim 1 wherein said effective amount ranges from about 1 milligram to about 25 grams of said composition per week.

18. The method of claim 1 wherein said effective amount ranges from about 50 milligrams to about 10 grams of said composition per week.

19. The method of claim 1 wherein said effective amount ranges from about 100 milligrams to about 5 grams of said composition every other day.

20. The method of claim 1 wherein said effective amount is about 1 gram of said composition once a week.

21. The method of claim 1 wherein said composition comprises a lipophilic entity.

22. The method of claim 1 wherein at least one said fatty acid compound is a monoglyceride, a diacylglyceride, triacylglyceride, free fatty acid, or fatty acid ethyl ester.

23. The method of claim 1 wherein said composition is in the form of a pharmaceutical composition.

24. The method of claim 1 wherein said composition is in a foodstuff.

25. The method of claim 24 wherein said foodstuff is a fat or oil containing foodstuff.

26. The method of claim 25, wherein said foodstuff is selected from the group consisting of animal meat, ruminant animal meat, ruminant mammal milk, and vegetable oil.

27. The method of claim 24, wherein said foodstuff is selected from the group consisting of a vegetable starch, vegetable protein, vegetable fiber, and an emulsified salad dressing.

28. The method of claim 1 wherein at least one said fatty acid compound is selected from the group consisting of any geometric isomer of 9,11-octadecadienoic acid and 10,12-octadecadienoic acid.

29. The method of claim 1 wherein at least one said fatty acid compound comprises any geometric isomer of 9,11-octadecadienoic acid and any geometric isomer of 10,12-octadecadienoic acid, said 9,11-octadecadienoic acid and 10,12-octadecadienoic acid being present at about equal proportions on a weight by weight basis.

30. The method of claim 1 wherein at least one said fatty acid compound comprises any geometric isomer of 9,11-octadecadienoic acid.

31. The method of claim 1 wherein at least one said fatty acid compound comprises c9,11-octadecadienoic acid.

32. The method of claim 1 wherein at least one said fatty acid compound comprises any geometric isomer of 10,12-octadecadienoic acid.

33. The method of claim 1, wherein at least one said fatty acid compound comprises t10,12-octadecadienoic acid.

34. The method of claim 1 wherein at least one said fatty acid compound comprises at least three double bonds, wherein at least two of said double bonds are conjugated.

35. The method of claim 1 wherein at least one said fatty acid compound comprises at least four double bonds, wherein at least two of said double bonds are conjugated.

36. The method of claim 1 wherein said method is effective for reducing atherosclerotic plaques in an artery.

37. The method of claim 36 wherein said artery is selected from the group consisting of an aortic artery, a cerebral artery, a coronary artery, and a carotid artery.

38. The method of claim 1 wherein said mammal is a human.

39. The method of claim 1, wherein said method further comprises monitoring the atherosclerotic plaques in said mammal.

* * * * *